(12) United States Patent
Dicello et al.

(10) Patent No.: US 6,412,330 B1
(45) Date of Patent: Jul. 2, 2002

(54) ABRASION TESTER

(75) Inventors: Paul Thomas Dicello, Cuyahoga Falls; Ravindra Kulasekere, Copley; Robert Edward Daly, Jr., North Canton, all of OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/856,443

(22) PCT Filed: Nov. 25, 1998

(86) PCT No.: PCT/US98/25251

§ 371 (c)(1),
(2), (4) Date: May 22, 2001

(87) PCT Pub. No.: WO00/31511

PCT Pub. Date: Jun. 2, 2000

(51) Int. Cl.$^7$ ................................. G01N 2/56
(52) U.S. Cl. ............................................ 73/7
(58) Field of Search .................... 73/7, 865.6

(56) References Cited

U.S. PATENT DOCUMENTS

| | | | |
|---|---|---|---|
| 3,065,627 A | * 11/1962 | Ross .............................. 73/7 |
| 4,098,111 A | 7/1978 | Hardmark et al. ............... 73/9 |
| 4,253,913 A | 3/1981 | Chaudhuri ................... 162/198 |
| 4,404,840 A | 9/1983 | Burr et al. ........................ 73/9 |
| 4,573,362 A | 3/1986 | Amlani ..................... 73/862.04 |
| 5,230,757 A | * 7/1993 | Rundman et al. ........... 148/539 |
| 5,689,058 A | 11/1997 | Yuan ............................... 73/9 |

FOREIGN PATENT DOCUMENTS

| | | | |
|---|---|---|---|
| GB | 1092172 | 11/1967 | |
| JP | 0096530 | * 4/1989 | ..................... 73/7 |
| JP | 6308017 A | * 11/1994 | ..................... 73/7 |

* cited by examiner

*Primary Examiner*—Robert Raevis
(74) *Attorney, Agent, or Firm*—David E Wheeler

(57) ABSTRACT

An apparatus for measuring abradability of a sample comprises a rotating drum with a rough surface and a means for contacting a sample with the rough surface while the drum is rotating. The sample may be caused to rotate relative to the drum, and to translate across the drum while the drum is rotating. Environmental controls may be used to control the temperature and the atmospheric conditions of the test. In the method of the invention, energy consumed by contact between the sample and the drum, as well as the weight loss of the sample, may be measured.

9 Claims, 5 Drawing Sheets

ABRASION TESTER

TECHNICAL FIELD

The invention relates to method and apparatus for testing the abradability of materials.

BACKGROUND ART

For some products, the abradability of the materials used to make them is an important measure of their durability and wear characteristics. For example, the abradability of the rubber used to make tire tread gives an indication of the life of the tire in terms of mileage, and may be an indication of the tire's resistance to irregular wear. In U.S. Pat. No. 5,113,688, issued May 19, 1992, a laboratory traction test is described wherein abradability, although of not primary importance, is recognized as one of the components in the traction properties of the rubber. Some of the art cited as references in that patent, namely U.S. Pat. Nos. 1,327,838; 1,490,603; 2,058,805; 3,638,230; 3,982,427; and 4,275,600; relate to the abradability of rubber compositions.

Burr et al., in U.S. Pat. No. 4,404,840 teach a device for evaluating the abrasive wear of elastomeric o-ring materials. In the device, a segment of a small diameter o-ring is held in contact with a rotating cylindrical disk. The disk is mounted to rotate on its longitudinal axis, and the o-ring segment and the cylinder are immersed in an abrasive fluid. Abrasive particles in the fluid are pulled between the wear surfaces, causing removal of surface materials, especially that of the o-ring. The oring segment is weighed before and after testing, and the amount of wear is calculated. Service loads or pressure are simulated by means of a cable and weight system urging the o-ring against the wear disk surface by means of a lever arm pulley arrangement.

Yuan, in U.S. Pat. No. 5,689,058 teaches a friction-material evaluation apparatus, especially adapted for testing brake friction material. The apparatus has a movable table which carries both a variable-speed electric motor that drives a brake rotor, and a reversible electric motor that may be actuated to advance the brake rotor into friction contact with the test material with a normal force that correlates to the output torque of the reversible electric motor. A heater 60 is positioned in surrounding relation to the hub of rotor subassembly 52, and preferably includes a heat sensor which detects the rotor surface temperature.

In the prior art, abradability was measured by dragging or pushing a rubber sample over a rough surface such as sandpaper, under a certain load for a specific distance. The abradability of the rubber sample was measured by weighing the sample before dragging it over the rough surface, and weighing the sample after dragging it over the rough surface, and the abradability of the compound was indicated by the volume loss per unit energy input. Such tests were ordinaily carried out at room temperature, and temperature factors relating to abradability were not usually considered.

It is the object of the present invention to provide an apparatus whereby abradability of a compound can be measured under different loads, under different temperatures, and under different atmospheric conditions. Also, the abrasion surface may be varied using the apparatus of the invention so that a profile of a particular compound can be obtained relating to its abradability over a broad range of surfaces.

Other objects of the invention will be apparent from the following description and claims.

SUMMARY OF INVENTION

An apparatus for abrasion testing comprises a rotatable drum having abrasive means on its surface, a variable speed motor associated with the drum for varying the speed of the drum, a sample holder in close proximity to the drum for contacting a sample with the drum, and a force transducer associated with the sample holder for measuring the energy expended when a sample is in contact with the drum. The apparatus may further comprise an environmental chamber encompassing the drum and the sample for testing at different temperatures and different atmospheres.

In the illustrated embodiment, the apparatus further comprises rotating means for rotating a sample relative to the drum, and translating means for moving the sample axially with respect to the drum. Accordingly, at least three axes of motion of the sample relative to the drum are possible using the apparatus. All axes of motion can be used simultaneously, or testing can be carried out on one axis of motion, as desired.

A personal computer can be used for controlling the rate of rotation of the drum, the speed of translation of the sample, and the speed of rotation of the sample. The personal computer can also be used to control the temperature and/or atmosphere in the environmental chamber.

The abrasive means of the drum may comprise an abrasive pattern etched, carved, stamped or molded onto the surface of the drum, and in one embodiment comprises a 10 to 300 mesh abrasive paper attached to said drum.

Load means may be provided for varying the load on said sample from 1 N to 25 N.

The temperature control means may control the temperature surrounding the drum and the sample from −100 C.° to 200 C.°.

Also, the atmosphere control means may provide an atmosphere surrounding the drum and sample comprising substantial amounts of a gas selected from the group comprising ozone, air, and water vapor.

The variable speed motor drives the rotation of the drum at from 2 to 100 revolutions per minute (rpm).

The force transducer is a multiaxial force transducer capable of measuring energy expended between the drum and the sample in multiple directions. In the illustrated embodiment, the multiaxial force transducer is capable of measuring energy expended in the direction of rotation of the drum and in a direction perpendicular to the rotation of the drum.

In the illustrated embodiment, the sample rotating means is a cable wrapped around a spindle carrying the sample, and the rotating means has associated therewith a variable speed control for varying the speed of rotation of the sample.

Also provided is a method for measuring the abrasive properties of a material comprising the steps of (a) providing an apparatus having a rotatable drum having abrasive means on its surface, a variable speed motor associated with the drum for varying the speed of the drum, a sample holder in close proximity to the drum for contacting a sample with the drum, and a force transducer associated with the sample holder for measuring the energy expended when a sample is in contact with the drum, (b) weighing a sample to determine its initial weight, (c) bringing a sample into contact with the drum at a specified load and a specified speed, (d) measuring the energy expended between the sample and the drum, (e) removing the sample from the test apparatus after a specified period of time and weighing the sample, and (e comparing the weight of the sample after testing with the initial weight of the sample.

In the method the sample may be rotated while the sample is in contact with a rotating drum.

The method may further comprise the steps of (a) providing the apparatus with an environmental chamber capable of controlling temperature and or atmosphere encompassing the drum and the sample, (b) repeating steps a–f above under different environmental conditions, and (c) comparing results achieved under different conditions for the same sample and for comparison samples.

The method further comprises the steps of comparing data with respect to weight loss and energy expended to estimate wear and traction properties of a sample.

DETAILED DESCRIPTION OF THE INVENTION

Figure 1:
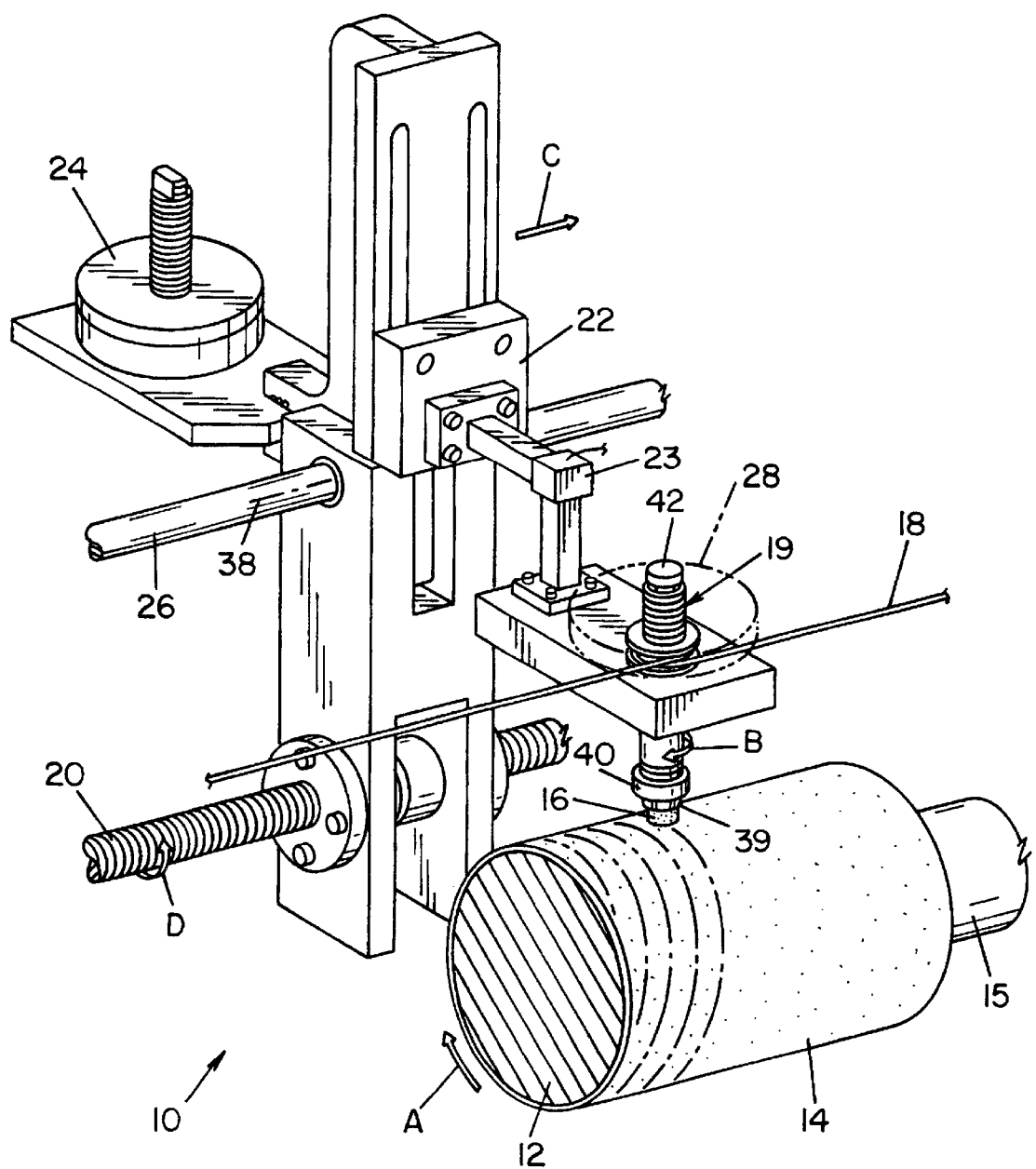
FIG. 1 illustrates the sample-carrying portion of the apparatus wherein a sample is in contact with a drum.
Figure 2:
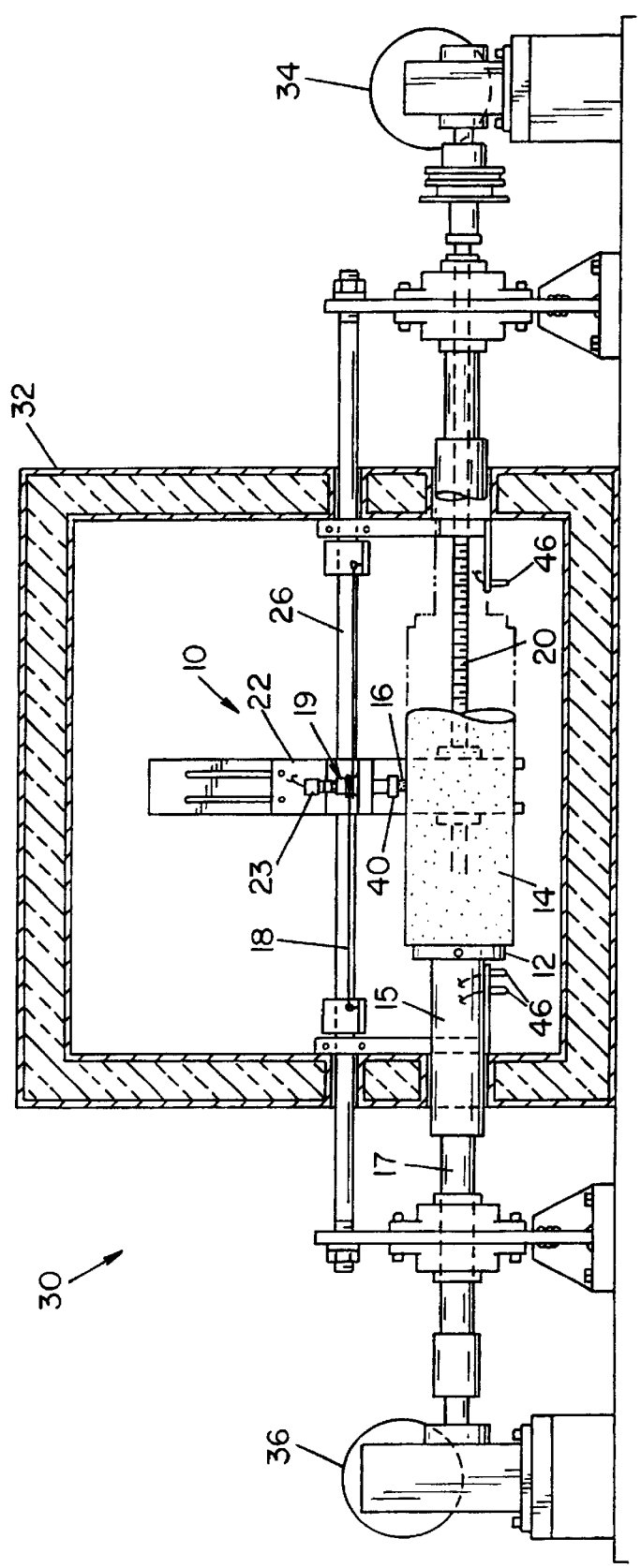
FIG. 2 is a front view of the apparatus, broken away to show the orientation of the parts.

With reference now to FIGS. 1 and 2, the sample-testing portion of the apparatus 10 comprises a drum 12 on which there is an abrasive surface 14. The drum rotates on axle 17. When a test is being carried out, a sample 16 is held in the apparatus in contact with abrasive surface 14.

In the illustrated embodiment, drum 12 is rotated in the direction of arrow 'a'. Those skilled in the art will recognize that the drum 12 may be rotated in either direction.

A test sample 16 is attached to spindle 19, and cable or wire 18 is wrapped around spindle 19 so that spindle 19 will rotate the sample 16 in the direction of arrow 'b' when the sample is translated on bar 26 in the direction of arrow 'c'. Again, those skilled in the art will recognize that translation in the opposite direction, and opposite rotation of the sample is possible.

Translation of the sample in the direction of arrow 'c' is caused by the rotation of threaded bar 20 in the direction of arrow 'd'.

Accordingly, when the apparatus is operated while cable 18 is attached to spindle 19, sample 16 will be moving relative to drum 12, based on the rotation of drum 12 in the direction of arrow 'a', rotating in contact with drum 12 by the rotation of the sample in the direction of arrow 'b', and moving laterally on drum 12 because of the translation of the sample holder 22 in the direction of arrow 'c'. The length of the sample path, and the amount of rotation of the sample 16 relative to rotation of the drum 12, is dependent on the relative speed of the drum and the relative translation speed of the sample. These parameters can be varied, e.g. translation of sample 16 with no rotation of drum 12, or rotation of drum 12 with no translation of sample 16, when different mechanisms or components of abrasion are being studied.

Those skilled in the art will recognize that when cable 18 is removed, and the sample locked, sample 16 will be translated without rotation of spindle 19.

Weight 24 is a counter balance, and is used to zero the pressure on sample 16, i.e., weight 24 counterbalances the weight of force transducer 23, spindle 19, and the connecting materials which are used to hold sample 16 in the apparatus. Weight 28 is used to provide the load on the sample against abrasive surface 14. Weight 28 may be varied from 1 to 25 newtons (N), and the variations in the load can be used to obtain a profile of the sample, i.e., to determine its abradability under different loads.

While a sample is being tested, data is collected by multiaxial force transducer 23 which measures the energy expended between the sample and the abrasive surface 14. The data collected by force transducer 23, and the weight loss of the sample can provide much information regarding the abradability of the sample as well as its traction characteristics. For example, if the energy measurements collected by force transducer 23 are high, and the abradability shown by the weight loss is low, this indicates that the compound has good traction properties and also has desirable wear properties.

Multiaxial force transducer 23 obtains data based on the tensile forces detected by the transducer. The transducer measures the change in resistance caused by the deformation of the transducer 23 as a result of friction between the sample and the abrasive surface. In the illustrated embodiment, a multiaxial force transducer provided by Hitec Corporation, 65 Power Rd., Westford, Mass., was used.

With reference now to FIG. 2, apparatus 30 includes motor 36 for controlling the rotation of drum 12, and motor 34 for controlling the lateral movement of sample holder 22 using screw shaft 20. Drive axle 17 is smaller than sleeve 15 to make it possible for easy replacement of the drum in the apparatus. Accordingly, sleeve 15 is slideable relative to shaft 17 but is provided with means for engaging shaft 17 (not shown) for the drive operation provide by motor 36. Easy replacement of the drum 12 makes it possible to obtain sample profiles using different drums with different etched surfaces. Also, removal of the drum from the apparatus makes easier the replacement of abrasive surfaces on the drum when such surfaces are separate from the drum. Drum 12 may be steel and the steel surface of the drum may be etched or engraved with specific patterns designed to test specific abradability parameters. Also, drums may be made of concrete, coated with asphalt or other surfaces that simulate road surfaces. Likewise, abrasive surfaces, such as sand paper, emery paper, and other similar abrasives having a 10 to 300 mesh may be held on the drum using adhesives, or other similar means. Also, blocks of material, optionally blocks of abrasive material, may also be bolted or attached to the drum in selected locations.

Environmental chamber 32 may be insulated to help control the temperature surrounding abrasive surface 14 and sample 16. Changes in temperature not only affect the properties of sample 16 but they also affect the properties of abrasive surface 14. Temperatures in the environmental chamber in the illustrated embodiment can be maintained at −100 degrees C. to +200 degrees C.

When environmental chamber 32 is properly sealed, conditions of abradability, and possibly traction, can be measured in ozone atmospheres and humid atmospheres. In order to carry out testing under consistent conditions, environmental chamber 32 may be used merely to control the humidity at a constant rate for a number of different samples.

Figure 3:
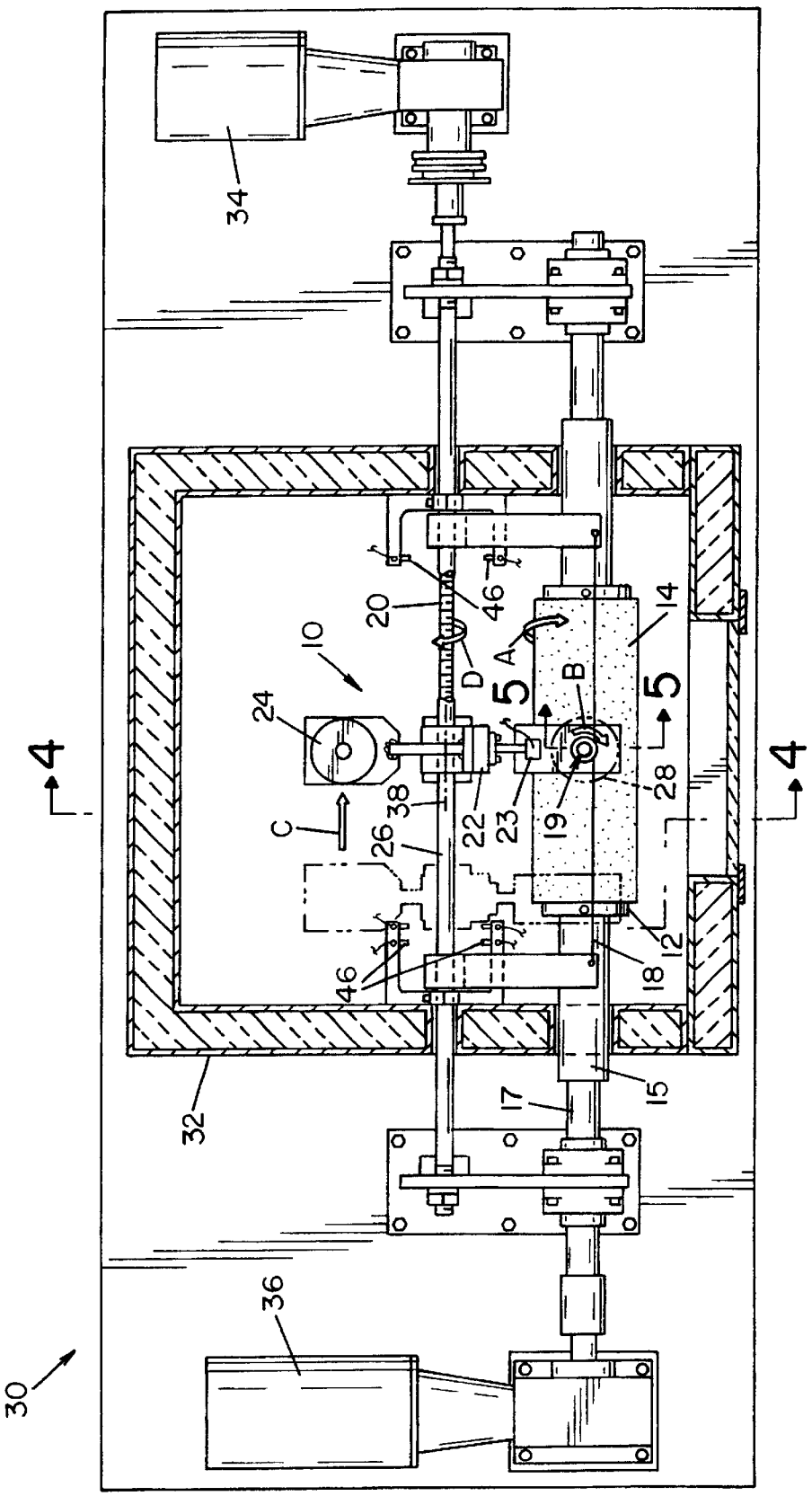
FIG. 3 is a top view of the apparatus, broken away to show the orientation of the parts.

With reference now to FIG. 3, a top view of the apparatus is illustrated showing in phantom lines the initial position of the testing portion of the apparatus 10, and by arrow C its translation to a position substantially in the center of the drum 12.

Light sensors 46 are used to sense when sample carrier 22 is at the end position and may be used as a signal to stop the apparatus when the end position is sensed. Light sensors 46 also serve as "homing" devices that can be used to reset the machine at the starting position if the need arises.

Figure 4:
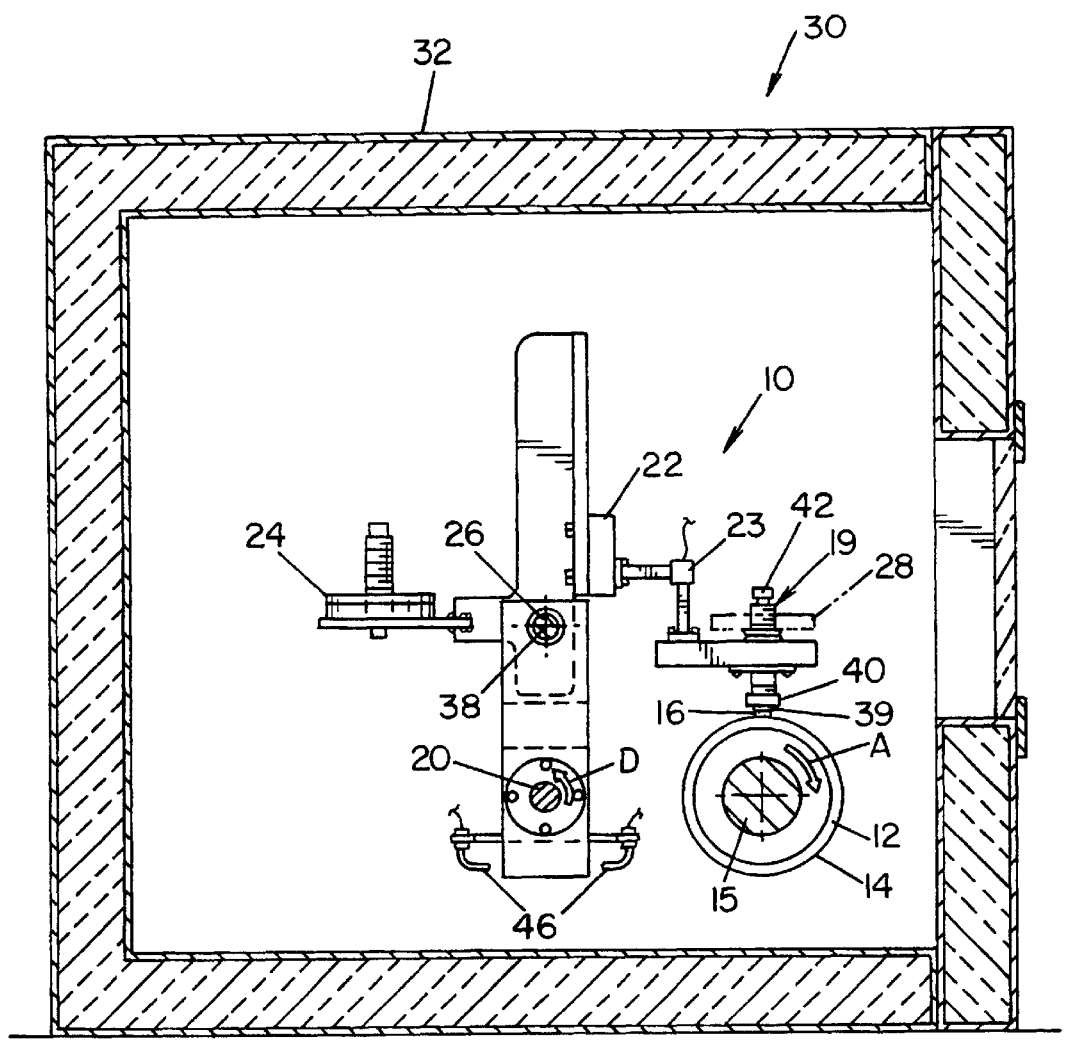
FIG. 4 is a side view of the environmental chamber, showing the sample in contact with the drum.

FIG. 4 illustrates a cross section of the apparatus taken along the lines 4,4 in FIG. 3.

Sample carrier 22 is rotatable on shaft 26 about pivot point 38, which provides a means for lifting sample 16 from abrasive surface 14, and providing clearance so that samples can be removed from and inserted into the apparatus.

Figure 5:
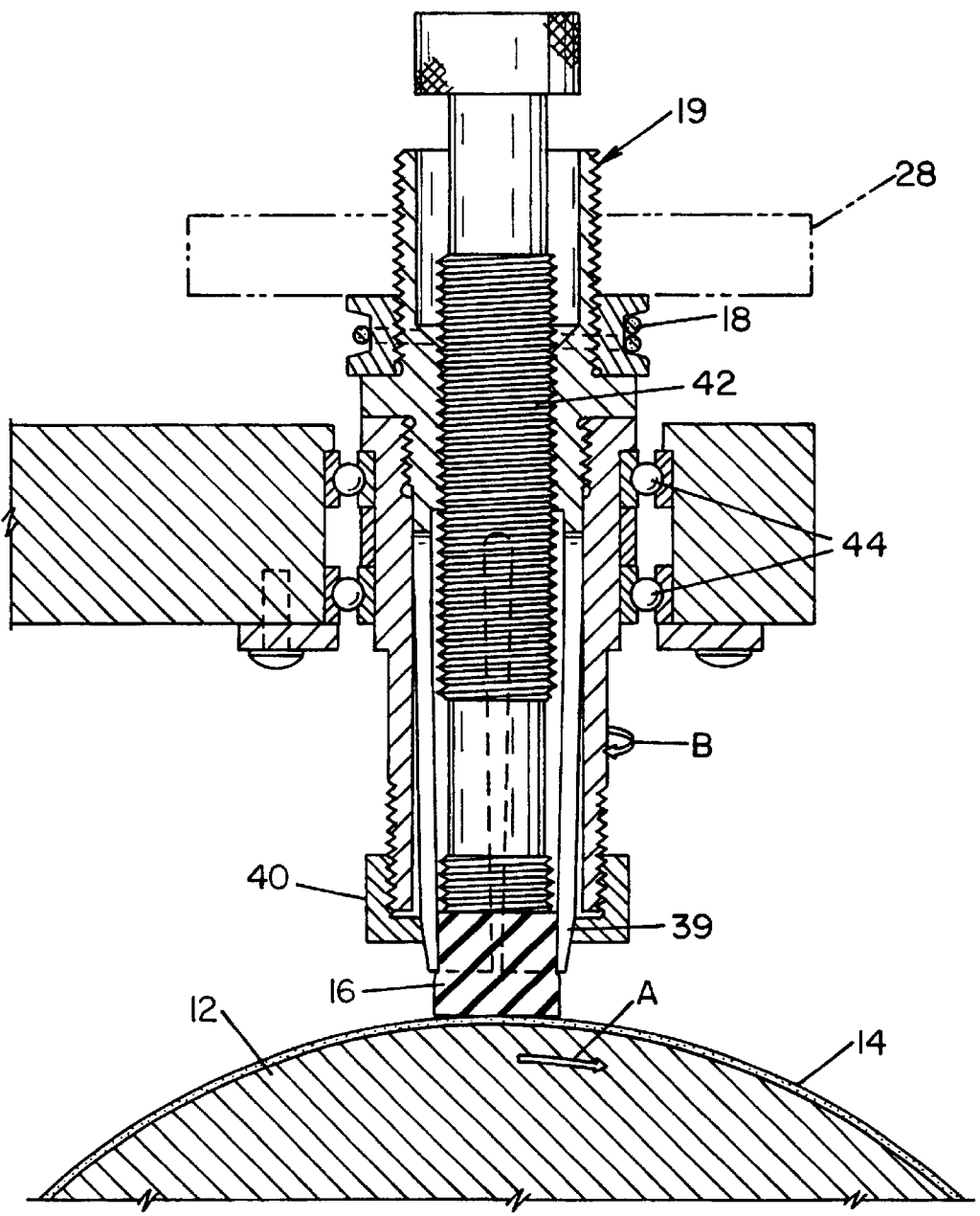
FIG. 5 is a close-up view of a sample holder, wherein a sample is in contact with the drum.

With reference now to FIG. 5, a cross-section of the apparatus along the lines 5,5 in FIG. 3 is shown. Sample 16 is held in collet 39, which is tightened by collet nut 40 when a sample 16 is loaded therein. Adjustable screw 42 is used to adjust the position of sample 16 in collet 39. In its operation in the illustration embodiment, tests are usually run when there are 2 millimeters exposure of sample 16 below the edge of collet 39.

Low friction bearings 44 are used on spindle 19 to minimize drag on the rotation of sample 16 caused by cable or wire 18. Minimal friction on spindle 19 is desirable so that the measurements obtained by multiaxial force transducer 23 are more directly related to the energy expended between sample 16 and rough surface 14 when a test is being carried out.

EXAMPLE

The following illustrates in detail how the apparatus of the invention is used when emery paper is used as an abrasive.
1. Scope
    1.1 This test measures the abrasion resistance of a test compound relative to a standard compound using emery paper applied to a rotating drum. The test specimens are rotated as they traverse the emery paper.
    1 2 Frictional forces generated by the abrading sample can be measured in the circumferential (x) and axial (y) directions using a custom designed load cell.
    1.3 The abrasion test is enclosed in an environmental chamber allowing the test to be conducted under various atmospheric conditions and temperature ranges (−100° C. to 200° C.).
2. Summary of Test Method
    2.1 A test specimen traverses, under constant pressure, temperature and speed, a defined abrasion distance across an abrasive sheet attached to surface of a rotating cylinder. The loss in weight is then determined. The abrasiveness of the sheet is determined using a standard elastomer which must fall within a specific range. The loss in weight of the elastomer under test is converted to volume loss from its calculated density, and the volume loss then referred to a specific nominal abrasive value.
3. Apparatus and Materials
    3.1 Boring bit, used to prepare a cylindrical test piece 16 mm in diameter.
    3.2 Abrasion tester modified from specifications in DIN 53516. The tester consists of a laterally movable test piece holder mounted on a bi-axial load cell and a rotating cylinder to which emery cloth is affixed. The entire assembly is enclosed in an environmental chamber.
    3.3 Emery cloth, corundum grain size 60, or as etched on drum surface. 3.4 Standard elastomer, can be ordered in 8×116×182 mm sheets, per DIN 53516.
    3.5 Balance, precise to 1 mg. and a densimeter for density measurement.
4. Preparation of Abrasive Cloth
    4.1 The emery cloth is firmly attached to the cylinder by means of three evenly spaced strips of double sided tape (about 50 mm wide) and extending along the complete length of the cylinder. The gap between the ends should be less than 2 mm. The direction of rotation should be marked on each abrasive cloth.
    4.2 The emery cloth is received with an abrasive power of 240 to 250 mg. It is necessary to reduce the abrasive power to below the upper range of 220 mg. This may be accomplished by performing a test once (or twice) with a steel bolt substituted for the specimen (at the lowest possible load). DIN 53516 specifies a loss in weight between 180 and 220 mg for a path of 40 m. After each conditioning operation, the abrasive sheet must be thoroughly cleaned. Three tests should be performed using the standard elastomer.
5. Test Specimens
    5.1 Drill or cure three specimens, at least 6 mm thick, from each test block. 7.
    5.2 The test can be run from left to right and vice versa. If for any reason the tests need to be run from left to right only, the machine needs to be "homed" after each test using the PC. When "homing", lift the specimen holder off the abrasive drum.
    5.3 The test is performed under conditions, −100° to 200° C., and not sooner than 16 hrs. after curing.
    5.4 Two samples are tested for each experimental compound if they are within +/−6 mg. If not, a third sample is tested and the average of the specimens that are within +/−6 mg is reported.
6. Calculation
    6.1 To calculate the abrasion, the average loss in mass shall be converted into volume loss from the density of the experimental compound, the volume loss being corrected by the deviation of the abrasive grade of the test abrasive cloth from the nominal abrasive grade (200 mg).

$$\text{Relative volume loss (mm3)} = \frac{\text{avg wt loss (in mq) of sample} * 200}{\text{avg wt loss (in mg) of std.} * \text{sp gr}}$$

Specific gravity may be in mg/mm3 or g/cm3.

While specific embodiments of the invention have been specifically described, those skilled in the art will recognize that the invention may be variously modified and practiced without departing from the spirit of the invention. The scope of the invention is limited only by the following claims.

What is claimed is:

1. An apparatus for abrasion testing comprising
    (a) a rotatable drum having abrasive means on its surface
    (b) a variable speed motor associated with said drum for varying the speed of said drum
    (c) a sample holder in close proximity to said drum for contacting a sample with said drum
    (d) rotating means for rotating a sample relative to said drum and translating means for moving said sample axially with respect to said drum, and
    (e) a transducer associated with said sample holder for measuring the energy expended when a sample is in contact with said drum, said apparatus being characterized by an environmental chamber encompassing said drum and said sample, wherein said environmental chamber has temperature control means which are provided to control the temperature surrounding said drum and said sample from −100 C.° to 200 C.°, and said environmental chamber has atmosphere control means adapted to provide an atmosphere surrounding said drum and sample comprising substantial amounts of a gas selected from the group comprising ozone, air, water vapor and mixtures thereof.

2. The apparatus of claim 1 wherein said rotating means has associated therewith a variable speed control for varying the speed of rotation of said sample.

3. The apparatus of claim 1 which further comprises a personal computer for controlling the rate of rotation of said drum, the speed of translation of said sample, and the speed of rotation of said sample, and said personal computer is used to control the temperature and/or atmosphere in said environmental chamber.

4. The apparatus of claim 1 wherein said abrasive means comprises an abrasive pattern etched, carved, stamped or molded onto the surface of said drum.

5. The apparatus of claim 1 wherein said abrasive means comprises a 10 to 300 mesh abrasive paper attached to said drum.

6. The apparatus of claim 1 wherein said transducer is a multiaxial force transducer capable of measuring energy expended between said drum and said sample in multiple directions.

7. The apparatus of claim 6 wherein said multiaxial transducer is capable of measuring energy expended in the direction of rotation of said drum and in a direction perpendicular to the rotation of said drum.

8. A method for measuring the abrasive properties of a material comprising the steps of
   (a) providing an apparatus having a rotatable drum having abrasive means on its surface, a variable speed motor associated with said drum for varying the speed of said drum, a sample holder in close proximity to said drum for contacting a sample with said drum, and a transducer associated with said sample holder for measuring the energy expended when a sample is in contact with said drum,
   (b) weighing a sample to determine its initial weight
   (c) bringing a sample into contact with said drum at a specified load and a specified speed
   (d) removing said sample from the test apparatus after a specified period of time and weighing said sample
   (e) comparing the weight of said sample after testing with the initial weight of said sample, said method being characterized by the steps of
   (f) measuring the energy expended between said sample and said drum
   (g) providing said apparatus with an environmental chamber capable of controlling temperature and or atmosphere encompassing said drum and said sample, and
   (h) rotating said sample while said sample is in contact with a rotating drum.

9. The method of claim 8 comprising the further steps of
   (a) repeating steps a–f of claim 8 under different environmental conditions, and
   (b) comparing results achieved under different conditions for the same sample and for comparison samples.

* * * * *